United States Patent [19]

Rugen

[11] 4,247,721

[45] Jan. 27, 1981

[54] PROCESS FOR PURIFICATION OF P-ISOPROPYL PHENOL

[75] Inventor: Donald F. Rugen, Wilmington, Del.

[73] Assignee: Sun Oil Company of Pennsylvania, Philadelphia, Pa.

[21] Appl. No.: 91,639

[22] Filed: Nov. 5, 1979

[51] Int. Cl.³ .................... C07C 37/74; C07C 39/06
[52] U.S. Cl. .................................... 568/756; 568/781
[58] Field of Search ................ 568/756, 771, 781

[56] References Cited

U.S. PATENT DOCUMENTS

| | | | |
|---|---|---|---|
| 2,529,209 | 11/1950 | Ayo et al. | 568/756 |
| 2,676,912 | 4/1954 | Maisel | 568/756 |
| 4,054,611 | 10/1977 | Nimaki et al. | 568/756 |

*Primary Examiner*—Werren B. Lone
*Attorney, Agent, or Firm*—J. Edward Hess; Donald R. Johnson; Paul Lipsitz

[57] ABSTRACT

A process for purifying p-isopropyl phenol (PIPP) by distilling the impure phenol at a pot temperature below about 475° F. under sufficient vacuum to permit separation of a heart cut, and washing the separated heart cut with liquid hydrocarbon containing from about 5 to about 10 carbon atoms.

8 Claims, No Drawings

PROCESS FOR PURIFICATION OF P-ISOPROPYL PHENOL p-Isopropyl phenol (PIPP) is a useful chemical intermediate for the organic synthesis of insecticides, antioxidants and pharmaceuticals. A source of PIPP is as a by-product in the production of hydroquinone where 1,4-diisopropylbenzene is oxidized. Because there is no efficient and economical means to obtain purified PIPP from the oxidation reaction mass containing numerous by-products, it has been common practice to separate the desired hydroquinone and dispose of the PIPP and other by-products present by burning or other wasteful means.

This invention now provides means to obtain high purity PIPP from its admixture with other materials, particularly with those by-products formed by oxidation of 1,4-disopropylbenzene to hydroquinone. In accord with the invention PIPP is produced in purified form by distilling the impure material at a pot temperature below 475° F. and under sufficient vacuum to distill over a heart cut at temperatures corresponding to about 410° to about 466° F. at 760 mm pressure and washing the heart cut with a low molecular weight hydrocarbon, i.e., a liquid hydrocarbon containing from about five to about ten carbon atoms.

As indicated, the process is of particular advantage for the separation of purified PIPP from its admixture with the by-products of 1,4-diisopropylbenzene oxidation. Normally such a mixture will contain about 60% to 65% by weight of PIPP. In accord with the process of the invention, this mixture is distilled under vacuum in conventional distillation equipment, a packed column being quite suitable. When the temperature rises and remains level, the desired fraction is separated, the distillation being carried out under sufficient vacuum to maintain the pot temperature below 475° F. in order to avoid decomposition of the PIPP to phenol and other materials.

It will be understood that the temperature at which the heart cut is taken will depend upon the pressure of the distillation. Thus, for example when distilling at 100 mm Hg. pressure, the temperature will level off at about 284° F. and distillation of the heart cut may continue to about 334° F. At a pressure of 180 mm, the heart cut fraction is taken from about 317° F. to 368° F. Thus, as is understood in the art the equivalent distillation temperature at 760 mm pressure will be about 410° to about 466° F.

The distillate fraction obtained in this way contains PIPP in about 90% to 96% purity and melts over a range of 48° to 57° C. Yield is about 50% to 60% PIPP. This still very impure fraction is then washed with a liquid aliphatic hydrocarbon. The liquid hydrocarbon will be one containing from about five to about ten carbon atoms and will be used at about room temperature or colder, preferably at about 5° to about 50° F. The isomeric pentanes, and hexanes are particularly suitable hydrocarbons. A single wash will increase the PIPP purity to about 98% PIPP purity and additional n-pentane washings may be used to obtain higher purity.

In order to further illustrate the invention the following examples are given:

EXAMPLE 1

A crude PIPP mixture obtained from the oxidation of p-isopropylbenzene containing 62.5% PIPP by weight was distilled in a packed column with 40 plates at 180 mm Hg. A heart cut fraction was taken over a boiling range of 317° F. to 368° F. This distillate contained 82% PIPP having a purity of 92% (m.p. 48°–57° C.). The distillate was washed once with 40 volume percent of cold n-pentane (45° F.) to yield a solid product of 98.3% purity (m.p. 57°–62° C.). Recovery of PIPP from the heart cut was 90% and 74% from the crude starting material. Two additional n-pentane washes yielded PIPP of 99.9% purity.

EXAMPLE 2

A crude PIPP mixture from the oxidation of p-isopropylbenzene containing 62% by weight of PIPP was distilled in a 40 plate packed column run at 20 plates at a reflux ratio of 5:1 and at 100 mm Hg. The forecut taken at temperatures up to 284° F. contained only 0.4% PIPP while the heart cut at 284° to 334° F. contained 84% PIPP at 87.3% purity. The heart cut was washed with 40 volume of mixed pentanes at 75° F. to yield a 77.2% recovery of PIPP having 98.5% purity (m.p. 61.5° F.).

EXAMPLE 3

When the details of Example 1 were repeated, but using a mixture of hexanes as the washing liquid, similar purification of the PIPP was obtained.

As is evident from the above, the process of the invention yields a high purity PIPP product not easily obtainable heretofore. Although distillation of phenols is, of course, known in the art, the product of a PIPP distillation has heretofore been limited to a purity of about 96% or less, probably due to impurities which were always codistilled. The present invention provides an economical means to recover high purity PIPP from hydroquinone manufacture and thus is a valuable advance to the art.

The invention claimed is:

1. A process for recovering high purity p-isopropyl phenol from its admixture with by-products obtained in the oxidation of 1,4-diisopropylbenzene to hydroquinone which comprises vacuum distilling said by-product mixture below a pot temperature of about 475° F. to obtain a heart cut distillate fraction and washing said heart cut with a liquid aliphatic hydrocarbon containing from about five to about ten carbon atoms.

2. The process of claim 1 where the liquid hydrocarbon is below room temperature.

3. The process of claim 2 where the liquid hydrocarbon is pentane.

4. The process of claim 2 where the liquid hydrocarbon is hexane.

5. The process of claim 2 wherein the vacuum distillation is carried out at a temperature between about 410° and about 466° F. at 760 mm pressure.

6. The process of claim 1 wherein the distillation temperature range is equivalent to 410° to 466° F. at 760 mm pressure.

7. The process of claim 6 wherein the washing is carried out with cold pentane.

8. The process of claim 6 wherein the washing is carried out with cold hexane.